US005665056A

United States Patent [19]

Nakasugi et al.

[11] Patent Number: 5,665,056
[45] Date of Patent: Sep. 9, 1997

[54] WATER-CURABLE SUPPORTING BANDAGE

[75] Inventors: Nobuyasu Nakasugi, Kyoto; Takayuki Sekine, Kawaguchi, both of Japan

[73] Assignees: Alcare Co., Ltd., Tokyo; San-Apro Limited, Kyoto, both of Japan

[21] Appl. No.: 336,423

[22] Filed: Nov. 9, 1994

[30] Foreign Application Priority Data

Nov. 10, 1993 [JP] Japan .................................. 5-304755

[51] Int. Cl.⁶ .................................................. A61F 5/00
[52] U.S. Cl. ................................. 602/8; 602/6; 602/1
[58] Field of Search ............................ 602/1, 5, 6, 8; 604/367, 372

[56] References Cited

U.S. PATENT DOCUMENTS

| | | | |
|---|---|---|---|
| 4,156,067 | 5/1979 | Gould | 528/73 |
| 4,433,680 | 2/1984 | Yoon . | |
| 4,574,793 | 3/1986 | Lee et al. . | |
| 4,667,661 | 5/1987 | Scholz et al. . | |
| 4,748,974 | 6/1988 | Richter et al. | 602/8 X |
| 4,774,937 | 10/1988 | Scholz et al. | 128/90 |
| 5,180,632 | 1/1993 | Edenbaum et al. | 428/253 |
| 5,403,267 | 4/1995 | Pearce et al. | 602/8 |
| 5,423,735 | 6/1995 | Callinan et al. | 602/8 |
| 5,455,294 | 10/1995 | Sheng | 524/424 |
| 5,476,440 | 12/1995 | Edenbaum | 602/8 |

FOREIGN PATENT DOCUMENTS

| | | |
|---|---|---|
| 2 92 606 | 1/1982 | United Kingdom . |
| WO89/08463 | 9/1989 | WIPO . |

*Primary Examiner*—Vanitha M. Alexander
*Attorney, Agent, or Firm*—Haverstock, Garrett & Roberts

[57] ABSTRACT

A water-curable support bandage constitutes a flexible fabric coated with a water-curable polyurethane resin composition containing a polyurethane prepolymer consisting of a polyol and a polyisocyanate, a catalyst and a stabilizer, wherein the polyol contains a polyethylene glycol and a bisphenol system diol. The water-curable support bandage provides greater storage stability, working time adequate for application to a diseased or injured body part, adequate modeling time, and cures rapidly thereafter to achieve a weight bearing strength. In the polyol a polypropylene glycol can be substituted for the polyethylene glycol.

15 Claims, 1 Drawing Sheet

Fig. 1

WATER-CURABLE SUPPORTING BANDAGE

Applicants hereby claim foreign priority benefits under 35 USC § 119 of corresponding Japanese Patent Application Serial No. (Hei) 5-304755.

INDUSTRIAL FIELD OF UTILIZATION

The present invention relates generally to water-curable support bandages for immobilizing and treating injured and diseased parts of the body, and, more particularly, to a water-curable support bandage for use on surgical and orthopedic patients which has greatly improved storage and curing properties.

BACKGROUND OF THE INVENTION

Water-curable support bandages are generally well known in the art. Numerous such bandages are widely available in both tape and sheet form and are typically made from fabric material coated with a water-curable polyurethane resin composition. To use such bandages, the tape or sheet is contacted with water and applied to the injured or diseased part of a patient. The water-curable polyurethane resin composition applied to the fabric reacts with the water and cures or hardens so as to form a substantially rigid member. Such water-curable bandages have many advantages as compared with conventional plaster bandages using plaster of Paris and have been gradually taking the place of the conventional plaster bandages. Since the desirous physical properties and advantages of such bandages are due largely to the polyurethane resin component thereof, substantial research and development efforts have so far been made to improve the polyurethane resin compositions, as a result of which various kinds of such compositions are known at present, some of which are discussed in detail below.

In operation, upon contact with water, the polyurethane resin composition starts a curing reaction, such that the initially flexible water-curable support bandage will also begin to cure and harden. Thus, for instance, after application and of the water-curable supporting bandage to the injured or diseased body part of a patient, after some amount of time, it is no longer able to be rewound if in tape form, and cannot be changed or adjusted if it is in sheet form. As the curing reaction further proceeds, the support bandage comes to have such a strength such that its shape is not changed even if some load is applied to it, and when the curing reaction is completed, the supporting bandage comes to possess a still higher strength. In this regard, one requirement of a water-curable supporting bandage for orthopedic treatment is that it should cure in a short time, so that, in turn, the polyurethane resin composition is required to have a very high reactivity to moisture. On the other hand, it is desirable for the water-curable supporting bandage to possess a storage stability over a long period, such that, while it is preserved or stored, for instance, in a hermetically sealed container, its does not proceed to cure.

As a practical example, the process for applying a water-curable supporting bandage to an injured or diseased part of a patient can include the following steps:

(1) the step of applying the water-curable supporting bandage which is already contacted with water to the diseased body part (the time period available for this will hereinafter be referred to as the "working time");

(2) the step of shaping or modeling, the water-curable supporting bandage which has thus been applied to the diseased part (this time period will hereinafter be referred to as the "modeling time");

(3) the step of maintaining or keeping the thus modeled water-curable supporting bandage until its curing proceeds into the state in which a load can be applied thereto (this time period will hereinafter be referred to as the "weight-bearing time"); and (4) the step in which the curing of the water-curable supporting bandage further proceeds into a perfectly cured state.

After examining the relationship between the strength of a water-curable supporting bandage which has undergone the above-identified steps and time, the following becomes clear. With regard to step (1), that is, the step of wrapping the water-curable supporting bandage or applying it on the diseased part, if the diseased part has a particularly complicated shape, a certain length of time is required for the application of the water-curable supporting bandage. If, during this period, the curing of the water-curable polyurethane resin composition proceeds too fast and, thus, the water-curable supporting bandage cures too fast, then it can become virtually impossible for the water-curable supporting bandage to be correctly applied in the required position. Therefore, during the shortest possible length of time which is considered to be necessary for applying the water-curable supporting bandage, the strength of the water-curable supporting bandage should desirably be kept as low as possible. For instance, for some applications the working time required should desirably be as short as from about 2.5 minutes to about 3.5 minutes, although such time can vary with the degree of skill of the doctor or technician applying the bandage and the part of the patient's body to which the bandage is applied.

Next, with regard to step (2), in the case wherein the water-curable supporting bandage applied in step (1) requires at least some modeling for proper positioning and supporting the body part, and the strength of the water-curable supporting bandage is maintained at a low value for an excessively long time, then it follows that, even when using some degree of force to model the water-curable supporting bandage to the correct shape, the water-curable supporting bandage may have a tendency to return somewhat to its original shape before it cures sufficiently to retain the modeled shape, due at least in part, to the inherent tendencies of the water-soluble supporting bandage to retain its original shape, and/or the elasticity of the patient's body. When this occurs, too much time and labor can be required for finishing the final modeling of the water-curable supporting bandage. Therefore, it is desirable that, only after the application of the water-curable supporting bandage, the strength thereof should greatly increase.

With regard to step (3), when the modeling is complete, and the water-curable supporting bandage is generally disposed in the correct position, it may still be necessary to keep the diseased part of the patient immovable until the water-curable supporting bandage cures into such a state that an ordinary load can be applied thereto. Therefore, the strength of the water-curable supporting bandage, once modeled, should desirably increase as fast as possible.

Further, with regard to step (4), in order to shorten the time during which both the patient and the doctor must be engaged or involved in the medical treatment, it is desirable for the water-curable supporting bandage to perfectly cure or harden as soon as possible and for the strength of the thus cured supporting bandage to reach the highest possible value. That is, it is ideal for the water-curable supporting bandage to possess such a curing reaction characteristic that the strength of the water-curable supporting bandage can be kept at a low value during the manipulation period during which the water-curable supporting bandage is applied to the diseased part, and then, during the subsequent modeling period, said strength can abruptly increase and keep sharply increasing thereafter to bring the water-curable supporting bandage into a perfectly cured state, thus finally reaching a high strength load bearing capability.

Prior Art

In connection with the above-mentioned requirements, several observations can be pointed out concerning a number of known polyurethane resin compositions used in conventional water-curable supporting bandages. For instance, in Japanese Unexamined Patent Application publication No. Sho 54-100181, there is disclosed a resin composition consisting of 10 to 70 percent by weight of a —NCO group-containing prepolymer which is obtained by reacting a polymer compound containing a hydroxyl group, an active methylene group or a primary or secondary amino group with an oxycarbonyl isocyanate-free multifunctional isocyanate, and 30 to 90 percent by weight of a low-viscosity isocyanate monomer or oligomer containing two or more —NCO groups within a molecule. This resin composition, which contains no catalyst, has the drawback that it is slow in curing, although it has an excellent storage stability. In Japanese Unexamined Patent Application Publication No. Sho 57-148951, there is disclosed a polyurethane resin composition which contains a prepolymer having isocyanate groups at the terminals thereof and two or more functional groups and a catalyst, wherein the prepolymer is a water-absorbing prepolymer, and the catalyst is soluble in water but insoluble in the prepolymer. This polyurethane resin composition is improved but still insufficient in respect of the curability or curing characteristics, and moreover, this polyurethane resin composition is inferior in storage stability, which is another disadvantage. In Japanese Unexamined Patent Application Publication No. Sho 58-146351, there is disclosed a resin which comprises an aromatic polyisocyanate and a polyol at an equivalent ratio of 2:1 to 15:1 and which contains, as a catalyst, dimolpholinodiethylether of 0.1 to 10 percent by weight based on the prepolymer. This polyurethane resin composition is excellent in respect of storage stability and curability, but has the drawback that it cures very fast, allowing only a short working time. Japanese Unexamined Patent Application Publication No. Sho 62-87162 discloses a curable resin containing a hydrophilic group covalently bonded to a curable resin or a lubricant such as an additive which is not compatible with the curable resin, so that the dynamic friction coefficient of the surface of the curable resin is set at 1.2 or less. This curable resin is directed to preventing the resin composition from tackily sticking at the time of medical treatment. Since the prepolymer in this case is a prepolymer which is composed mainly of polypropylene glycol, a large amount of catalyst must be used in order to enhance the curability, and the working time is relatively short, which is the drawback of this resin composition. Japanese Unexamined Patent Application Publication No. Sho 62-172008 proposes a polyurethane prepolymer composition containing a polyurethane prepolymer and a tertiary amine catalyst and, in addition, methanesulfonic acid as a stabilizer. This composition is improved with respect to storage stability but has the drawback that the composition sticks to the operator's gloves and needs to contain a relatively large amount of the catalyst. In Japanese Unexamined Patent Application Publication No. Hei 3-41116, there is proposed a polyurethane resin composition which comprises a polyurethane prepolymer consisting of a polyol and a polyisocyanate, a catalyst, a stabilizer and an ester compound of a polyethylene glycol. This composition is lessened in the degree of tack and sticking to the operator's gloves but is not satisfactory in respect of the curing characteristics. In Japanese Unexamined Patent Application Publication No. Hei 3-503611, there is proposed an isocyanate functional resin which contains the respective residues of (a) a polyethylene glycol, (b) a triol or a tetrol having a molecular weight of 200 or less, and (c) an aromatic isocyanate, wherein the weight ratio between (a+b) and (c) is 1:1 or less. This resin has a low adhesion and an excellent curing characteristics, but, since a low-molecular and tri- or higher-functional polyol is used, the resin has the drawback that the storage stability and the working time thereof are inferior. In Japanese Unexamined Patent Application Publication No. Hei 4-120117, there is proposed a polyurethane resin composition which comprises a polyol and a polyisocyanate, wherein, as the polyol, there is used a specific bisphenol system diol of at least 1 percent by weight based on the components of the polyol. This polyurethane resin composition is further improved in respect of the storage stability but remains unsatisfactory in respect of the curing characteristics.

Problems that the Invention is to Solve

The many known polyurethane resin compositions which are so far known and proposed have both advantages and disadvantages as pointed out above, and thus, there has not been yet obtained a polyurethane resin composition which is satisfactory in respect of both the storage stability and the curing characteristics thereof, namely, that the composition can be stored for a relatively long time under normal conditions; that it allows adequate time for application of the bandage on an injured or diseased body part; that it enables the bandage to retain its shape once modeled; and thereafter cures to its maximum weight bearing strength as soon as possible.

OBJECTS AND SUMMARY OF THE INVENTION

It is therefore an object of the present invention to provide a water-curable supporting bandage which can be stored for a long period of time prior to use without significant reduction or degradation in the desired properties thereof.

Another object of the present invention is to provide a water-curable supporting bandage that once contacted with water allows adequate working time for application to an injured or diseased body part before curing or hardening of the bandage.

A more particular object of the present invention is to provide a water-curable bandage which has a working time for application in a range from about 2 to about 3 minutes.

Another object of the present invention is to provide a water-curable supporting bandage that allows adequate time for modeling to the shape of an injured or diseased body part, yet which thereafter rapidly begins to cure and harden so as to retain the modeled shape.

Another object of the present invention is to provide a water-curable supporting bandage that once modeled rapidly achieves a weight bearing strength.

Another object of the present invention is the provision of a water-curable supporting bandage which produces only relatively low heat during the curing stages thereof.

In order to achieve the above-mentioned objects, the water-curable supporting bandage according to the present invention is constituted in such a manner that a flexible fabric is coated with a water-curable polyurethane resin composition which contains a polyurethane prepolymer consisting of a polyol and a polyisocyanate, a catalyst, and a stabilizer, wherein the polyol preferably contains a polyethylene glycol and a bisphenol system diol. The content of the polyethylene glycol and the bisphenol system diol in the polyol component is desirably at least about 50 percent by weight of the components of the polyol. The compounding proportion of the polyethylene glycol to the bisphenol system diol in the preferred polyol component can vary with the kind of the bisphenol system diol used, but should desirably lie within the range of from about 1:0.2 to about 1:5. This provides the desired storage stability and low heat production during the curing of the bandage. As an alternative, the polyol can include a polypropylene glycol instead of polyethylene glycol.

Water-curable support bandages constituted as described above have been found to provide all of the desired characteristics and properties sought therefore, including long storage stability without adverse effects on the curing characteristics thereof, even when stored under ordinary storage room conditions. Further, the present water-curable supporting bandage can provide a working time in a range from about 2 to about 3 minutes such that the bandage can be applies with ease even to complicated patient body parts where conventional bandages would be difficult to apply. In addition, once the working time as elapsed, the curing proceeds rapidly and the strength of the bandage increases, such that modeling of the bandage can be performed surely and the thus modeled shape is retained. Still further, after modeling the curing of the bandage proceeds rapidly so as to achieve a relatively high weight bearing strength in a short time, without the generation of harmful heat conditions.

Figure 1:
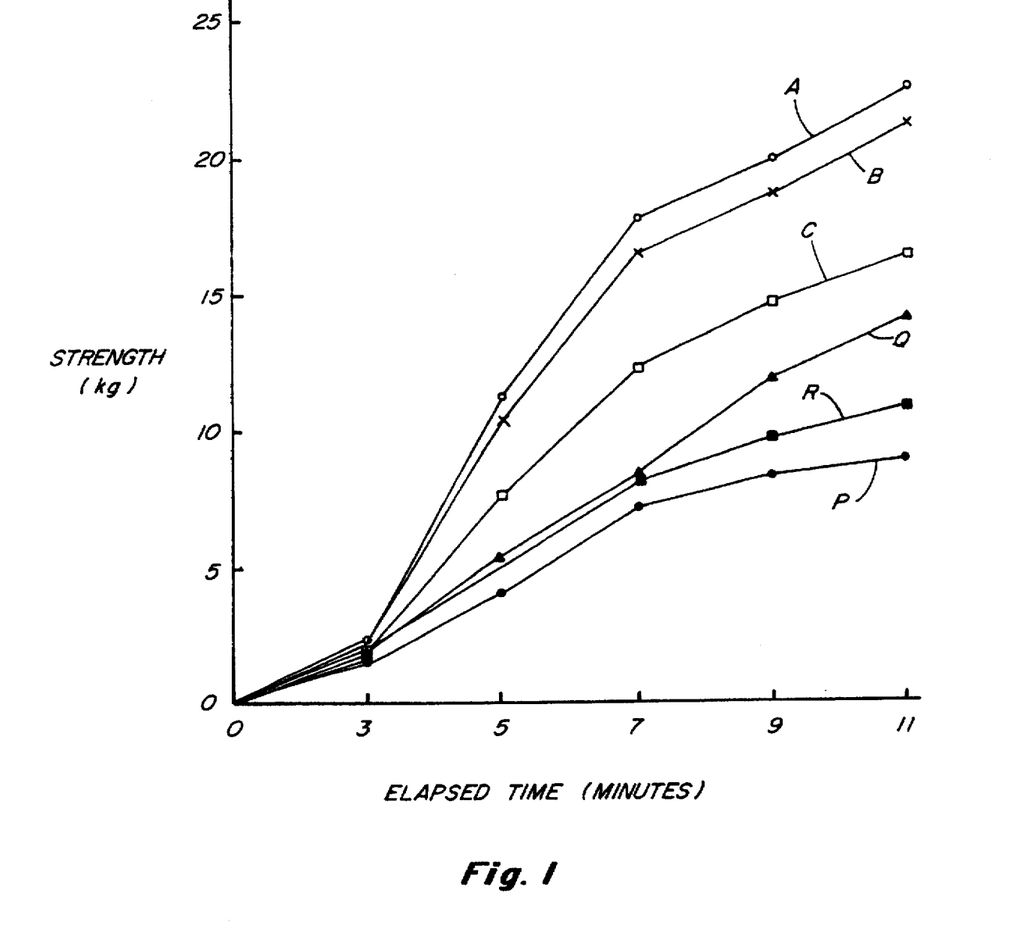
FIG. 1 is a graph showing the relationship between the strength and the lapse of time pertaining to the water-curable supporting bandages according to the selected Embodiments of the present invention described below and the several water-curable supporting bandages according to the Comparative Examples.

Explanation of Reference Symbols in FIG. 1

A . . . Characteristic curve of Embodiment 1 of the present invention.

B . . . Characteristic curve of Embodiment 2 of the present invention.

C . . . Characteristic curve of Embodiment 5 of the present invention.

P . . . Characteristic curve of Comparative Example 1.

Q . . . Characteristic curve of Comparative Example 2.

R . . . Characteristic curve of Comparative Example 3.

DETAILED DESCRIPTION OF THE PREFERRED EMBODIMENTS

The water-curable supporting bandage according to the present invention is constituted in such a manner that a flexible fabric is coated with a water-curable polyurethane resin composition which contains a polyurethane prepolymer consisting of a polyol and a polyisocyanate, a catalyst, and a stabilizer, wherein the polyol preferably contains a polyethylene glycol and a bisphenol system diol. The content of the polyethylene glycol and the bisphenol system diol in the polyol component is desirably at least about 50 percent by weight of the components of the polyol. The compounding proportion of the polyethylene glycol to the bisphenol system diol in the preferred polyol component can vary with the kind of the bisphenol system diol used, but should desirably lie within the range of from about 1:0.2 to about 1:5. If the compounding ratio is significantly outside of this range, the strength of the water-curable supporting bandage, and the storage stability thereof have been found to be lowered and the mount of heat produced during the curing thereof relatively great in many cases.

A wide variety of flexible fabrics can be used in the present invention and include knitted fabrics, woven fabrics and nonwoven fabrics. A wide variety of materials can be used for the fabrics such as those which have a low moisture regain and a high tensile strength and which are unreactive and wettable with the polyurethane resin composition. As examples, knitted fabrics, woven fabrics and nonwoven fabrics composed of, for instance, glass fibers, alamide fibers, polyester fibers, polyolefin fibers, polyamide fibers, polyacryl fibers, rayon fibers, or cotton fibers can be used. Of these fabric materials, a particularly suitable one is a fabric made in such a manner that aggregates (threads) of glass fibers or polyester fibers are raschel-knitted into a fabric with a thickness of from about 0.08 to about 5.0 mm and a mesh size of from about 3 to about 30 mesh/cm$^2$. For example, the base fabrics proposed by the present applicant in Japanese Examined Patent Application Publication No. Sho 63-5100, Japanese Unexamined Patent Application Publications No. Sho 60-242851, No. Hei 2-71746, and Japanese Patent Application No. Hei 3-194853, etc. can be used.

The preferred polyurethane prepolymers for use in the present invention include those which are obtained by reacting a polyol with a polyisocyanate and have isocyanate groups at the terminals.

The polyols in the present invention can include those which have a polyethylene glycol and a bisphenol system diol as components, but other polyols such as for instance polypropylene glycols, random or block copolymers of ethylene oxides and propylene oxides can also be used.

The polyethylene glycol (PEG) is obtained by admixing an ethylene oxide to an ethylene glycol at a temperature of from about 100° to about 180° C. in the presence of a catalyst. The average molecular weight of the polyethylene glycol is normally about 200 or higher, but a water-curable supporting bandage using a polyethylene glycol with a molecular weight smaller than about 1,000 tends to produce, when it cures, higher heat than a water-curable supporting bandage using a polyethylene glycol with a molecular weight larger than 1,000. Thus, a polyethylene glycol with a molecular weight less than about 1,000 should desirably be used in as small an amount as possible. On the other hand, in the case of a water-curable supporting bandage using a polyethylene glycol with a molecular weight higher than about 1,000, the rigidity thereof after it has cured is low. Therefore, the use of such a polyethylene glycol with a molecular weight higher than about 1,000 should also desirably be avoided in view of the rigidity characteristics thereof. As a result, it becomes necessary to select a suitable mixture of a low-molecular weight PEG and a high-molecular weight PEG in view of the generated heat and the rigidity. The polyethylene glycols generally commercially available have been found to often contain some amount of the catalyst which was used for the synthesis thereof. Therefore, it is generally necessary or preferred to remove such catalyst or neutralize it by adding a mineral acid, such as, for instance, sulfuric acid, hydrochloric acid, or a stabilizer to be described later.

As for the bisphenol series diol, it is generally obtained in such a manner that, to a bisphenol such as bisphenol A, bisphenol F, bisphenol B or the like, an alkylene oxide is added in the presence of a catalyst at a temperature of from about 100° to about 180° C. An alkylene oxide, an ethylene oxide, a propylene oxide, a butylene oxide or the like can be used. A suitable or desirable bisphenol system diol is the ethylene and/or propylene oxide adducts of bisphenol A. The number of moles of the alkylene oxide added to the bisphenol system diol is preferably 2 or more. The adduct of from about 2 to about 3 moles of ethylene oxide and the adduct of from about 2 to about 30 moles of propylene oxide are effective for an improvement in the storage stability of the polyurethane prepolymer. The amount of the bisphenol in the bisphenol system diol which is required for improving the storage stability of the urethane prepolymer composition is ordinarily about 2.5% or higher and, more preferably about 5% or higher, based on the polyurethane resin composition. If the amount of the bisphenol system diol is less than about 2.5%, the storage stability cannot be sufficiently improved. In the case of using the bisphenol system diol for purposes other than the improvement of the storage stability, bisphenol system diols with mole addition numbers outside of the range mentioned above can also be used.

The usable average molecular weight of the polyol obtained by blending a polyethylene glycol with a bisphenol system diol is from about 400 to about 2,000 and, more preferably from about 500 to about 800. A polyurethane resin composition using a polyol with an average molecular weight less than 400 has been found to be hard yet brittle when cured, and thus, it is not suitable for use in a supporting bandage. On the other hand, a polyurethane resin composition using a polyol with an average molecular weight of about 2,000 or higher may be too soft when it is cured and thus not suited in use for a supporting bandage either.

As the polyisocyanate, many hitherto known aromatic polyisocyanates can be used. Some more desirable polyisocyanates include, for instance, 4,4'-diphenylmethane diisocyanate, 2,4'-diphenylmethane diisocyanate, phenylene diisocyanate, polymethylene polyphenylene polyisocynate, and polyisocyanates modified by carbodiimide, etc. They can be used singly or in combination of two or more. Particularly desirable are 4,4'-diphenylmethane diisocyanate, 2,4'-diphenylmethane diisocyanate, and polyisocyanates modified by carbodiimide.

The compounding ratio of the polyol and the polyisocynate for obtaining a polyurethane prepolymer having isocyanate groups at the terminals thereof is normally from about 2 to about 5 equivalents, and more preferably from about 2.5 to about 5 equivalents, of the polyisocyanate per one equivalent of the polyol. The reaction between the two substances is achieved by stirring under heating, normally at from about 30° to about 100° C. and more preferably at from about 50° to about 80° C. The viscosity of the polyurethane prepolymer is normally from about 10,000 to about 50,000 centipoise (cps) and, more preferably from about 15,000 to about 40,000 cps, at room temperature.

As the catalyst, any of those catalysts having excellent storage stability can be used. Such catalysts which have hitherto been well known include catalysts such as dimolpholinodiethylether, bis(2,6 dimethylmolpholino) dietheylether, the substituted molpholinodiethylethers disclosed in Japanese Unexamined Patent Application Publication No. Sho 62-103071, etc. These catalysts all can be used singly or in the form of a mixture of two or more of them. As for the amount of the catalyst used, the catalyst is added in such an amount that the working time of the water-curable supporting bandage can become from about 2 to about 3 minutes. Normally, the amount of the catalyst is from about 0.1 to about 5.0 percent by weight, and more preferably from about 0.5 to about 3 percent by weight, based on the polyurethane resin composition. If the catalyst amount is less than this value range, the working time has been found to become too long, while conversely, if the catalyst amount is greater than this value range, the working time becomes too short.

As the stabilizer, benzoyl chloride, methanesulfonic acid or the like which has hitherto been known can be used. These stabilizers all can be used singly or in the form of a mixture of two or more of them. The amount of the stabilizer used is, although it varies with the amount of the catalyst used, normally from about 0.005 to about 1 percent by weight, and more preferably from about 0.01 to about 0.5 percent by weight, based on the polyurethane resin composition. If the amount of the stabilizer is less than about 0.005 percent by weight, no stabilization effect is obtained, while if the stabilizer amount is more than about 1 percent by weight, the activity of the catalyst is spoiled.

To the polyurethane resin composition according to the present invention, various kinds of additives such as an anti-foaming agent, an anti-oxidizing agent, a viscosity modifier, an adhesion inhibitor, an ultraviolet absorbing agent, a coloring agent such as a pigment or dye, a filler such as calcium carbonate, titanium dioxide, carbon black, clay, etc. can also be added as desired or required.

The polyurethane resin composition can be manufactured in such a manner that, to a urethane prepolymer obtained from a polyol and a polyisocyanate, a catalyst, a stabilizer, and various other additives are added, or, when the urethane prepolymer is to be manufactured, a catalyst, a stabilizer, and various other additives are partially or wholly added beforehand together with a polyol and a polyisocyanate.

The water-curable supporting bandage according to the present invention can be manufactured by coating a flexible fabric with a polyurethane resin composition using known methods such as, for instance, a method wherein, in a room adjusted to a low humidity, the polyurethane resin composition is applied onto the fabric by means of a rolling process. The thus formed water-curable supporting bandage can then be preserved in a hermetically sealed state in a moisture proof container so that when the bandage is to be applied to the diseased part of a patient, the container can be opened, the bandage contacted with water, and then applied to the diseased part.

Operation of the Invention

The curing reaction mechanism of the water-curable supporting bandage according to the present invention is not easily elucidated since various factors such as the kind and the amount of the catalyst, the reaction temperature, the hydrophilicity of the polyurethane resin composition, etc., can be varied and can interact in a relatively complicated manner. However, the curing mechanism can be better understood when the following observations are considered.

First, the polyethylene glycol as one component of the polyol in the polyurethane prepolymer is highly hydrophilic, so that, if the supporting bandage is dipped into water, then the amount of water necessary to cure the polyurethane resin composition quickly penetrates into the polyurethane resin composition, and the water uniformly spreads through the whole polyurethane resin composition, as a result of which the reaction of the water with the isocyanate groups takes place. The catalyst in the polyurethane resin composition promotes the reaction between the water and the isocyanate and, also, the curing thereof. Since the temperature of the polyurethane resin composition is raised due to the heat of reaction resulting from the reaction between the water and the isocyanate, the reaction speed or rate is further promoted, so that the water-curable supporting bandage cures in a short time. This process corresponds to the afore-said steps (2) and (3); and thus, it becomes possible to model the bandage correctly, and a weight-bearing capability is realized in a short time. Further, since the water necessary for the reaction can be retained in the surface of the supporting bandage, all the reactive groups react at about the same time, so that the reaction is completed in a short time, as a result of which a supporting bandage with a high strength is obtained. This corresponds to the afore-mentioned step (4).

A polyurethane prepolymer in which the polyol component thereof comprises only a polyethylene glycol is more hydrophilic as compared with a polyurethane prepolymer comprising a polypropylene glycol. Therefore, the former is more highly reactive with water, and the amount of the catalyst necessary for adjusting the curing time can be reduced. However, the resulting cured polyurethane resin is also hydrophilic and therefore retains the excess water content for long time, and the water-curable supporting bandage remains in a plasticized state until it is dried, and thus, the manifestation of its strength is delayed. Further, a polyurethane prepolymer comprising a polyethylene glycol is hydrophilic, and therefore, the reaction thereof with water is completed relatively early, so that there is the tendency that the heat of reaction concentrates, and the temperature rises due to the generated heat increases. In particular, in the case of a polyurethane prepolymer comprising a polyethylene glycol with a molecular weight of about 1,000 or less, the temperature reached when the prepolymer cures tends to become high. It is believed that the reason for this is related to the observation that, the lower the molecular weight of the polyethylene glycol used, the higher the heat of solution emitted when it dissolves into the water. Further, a polyurethane prepolymer formed from a polyethylene glycol is inferior in respect of the storage stability.

With reference to the abovementioned drawbacks, the bisphenol system diol used in the present invention can make an improvement without spoiling the advantages of using polyethylene glycol. In this regard, if a (hydrophobic) bisphenol system diol with a molecular weight of about 800 or less is used in place of the low-molecular polyethylene glycol, then the temperature reached in curing is lowered, and the manifestation of its strength can be quickened. This is believed to be due to the hydrophobicity resulting from the molecular structure of the bisphenol system diol. It has also been found that such bisphenol system diol does not dissolve into water and emits scarcely any heat when it is mixed with water. It is believed that the manifestation of the strength is due to the fact that said diol is hydrophobic and, at the same time, each have benzene nucleuses within the molecule, so that the strength is enhanced. Further, a compound composed in such a manner that a large amount of an ethylene oxide is added to a bisphenol can be used in place of the polyethylene glycol. Moreover, an alkylene oxide adduct with suitable mole number can improve the storage stability of the polyurethane resin composition.

Working Examples

Embodiments of the present invention will now be described in detail, as will Comparative Examples. The materials used for the polyurethane resin compositions according to the Embodiments of the present invention and those according to the Comparative Examples are shown in Table 1, while the formulae therefor are shown in Table 2. The properties of the polyurethane resin compositions obtained in accordance with such formulae and the product evaluations thereof in the form of the water-curable supporting bandages obtained by applying the polyurethane resin compositions to base fabrics are set forth in Table 3 and Table 4.

The polyurethane resin compositions of both the Embodiments according to the present invention and the Comparative Examples were all synthesized in the same manner as follows.

In a reaction vessel which had the atmosphere inside thereof evacuated and replaced with a nitrogen gas, a polyol component, an anti-foaming agent and an antioxidant agent were introduced; the water content was removed at a temperature of from about 80° to about 120° C.; and a portion of the stabilizer was added. Thereafter, a polyisocyanate component was added to effect a reaction at a temperature of from about 50° to about 90° C. Further, a catalyst and the remainder of the stabilizer were added, and the mixture was stirred for about one hour, whereby a polyurethane resin composition was obtained. This polyurethane resin composition was put into a hermetically sealed vessel which had its internal atmosphere previously evacuated and replaced with a nitrogen gas.

As for the formation of the water-curable supporting bandages, in the cases of both the Embodiments of the present invention and the Comparative Examples, the water-curable supporting bandages were all formed alike by applying the respective polyurethane resin compositions to the same base fabric. More particularly, in each case, a glass fiber of ECC751/01.0Z was raschel-knitted into a flexible fabric having a width of 10 cm, a density of 14 warps/inch and 15 wefts/inch, a METSUKE (weight per unit area) of 310 g/m$^2$, and the thus obtained tape-shaped raschel-knitted fabric was subjected to a heat cleaning. The application of the polyrethane resin composition to this fabric was carried out in a workroom maintained as a low-temperature environment at a rate of about 210 g/m$^2$ using a roll coater method. The fabric to which the resin was thus applied was wound up to a length of 1.8 m, whereby a water-curable supporting bandage was formed and enclosed in a moisture-impermeable bag wherein the atmosphere therewithin had been evacuated and replaced with a nitrogen gas.

The properties of the above-mentioned polyurethane resin compositions and the resultant water-curable supporting bandages were evaluated as follows in each case:

Viscosity

A sample of the polyurethane resin composition with its temperature adjusted to 20° C. was measured by a B type viscometer using a No. 4 rotor at a velocity of 12 rpm.

Storage Stability

About 50 ml of the polyurethane resin composition was collected in a 100 ml polypropylene bottle in a nitrogen gas atmosphere. The bottle was heremetically sealed, kept in a constant-temperature dryer with the temperature at 130° C., and the time until the fluidability of the polyurethane resin composition reached zero was measured.

Working Time

In a measuring room with its temperature adjusted to 25° C., a water-curable supporting bandage with the width of 10 cm was taken out from the moisture-impermeable bag, dipped into water having a temperature of 20° C. for 10 seconds and, after the water was lightly swished off from the supporting bandage, the supporting bandage was wound or rolled around a cylinder, and the time until the thus wound or rolled bandage could be no further wound or rolled was measured.

Heat Generation Temperature

In the measuring room with its room temperature adjusted to 25° C., a water-curable supporting bandage with a width of 10 cm was taken out from the moisture-impermeable bag and dipped into water having a temperature of 20° C., and then, the water was lightly swished off from the supporting bandage. Around a polyethylene container into which water was previously placed and warmed to 36° C., the subject water-curable supporting bandage was wound, and, on the third turn or layer of the thus wound bandage, a thermocouple was placed. Thereafter, the bandage was further wound so as to form three more rams or layers and the highest heat generation temperature of the bandage was measured using the thermocouple.

Variation in Strength due to the Lapse of Time

The rolled water-curable supporting bandage was taken out from the bag, and unrolled without applying any tension to it and cut to a length of 60 cm. Six such cut pieces of the supporting bandage were prepared in this manner and laid one on the top of another, taking care to ensure that the six bandage pieces would not shift in the width direction thereof and that the front surface of each piece would be opposed to the rear surface of the other adjacent piece. Then while in this state, the six pieces were enclosed into a bag which previously had the atmosphere therein evacuated and replaced with a nitrogen gas. The six pieces thus formed were used as a specimen on which the operations discussed next were performed. In this regard, it was considered that, in the operation carried out so far, the water component in the air might have reacted with the resin to some degree. Therefore, it was determined that the operation should be finished within about 2 minutes 30 seconds after the bag was opened. Further, it was determined that the bag should be opened in a room having a temperature of about 20° C., and a humidity of about 20% relative humidity (RH) or lower.

The strength measurements conducted on the above-prepared specimen were carried out in a measuring room in which the temperature was adjusted to 20° C. and the humidity was adjusted to 50 to 70% RH. The temperature of the specimen used was adjusted to 20° C. The specimen was placed on a metal net made of stainless steel and dipped, without stirring, into running water which was adjusted to 20° C. After 10 seconds, the specimen was calmly dram out from the water, and the specimen was shaken to swish off the extra water therefrom. A release paper was laid down on a testing stand (manufactured by EISSHIN Corporation) with its temperature adjusted to 30° C., and, on the release paper thus laid down, the specimen was placed and spread flat, taking care not to apply a pressure higher than necessary. In this step, care was taken to ensure that, between the respective adjacent laminated pieces of bandage constituting the specimen, no gap or clearance would be formed. On the specimen thus spread, another release paper was laid, and a weight was applied in such a manner that, after 60 seconds, a load of 500 g per 100 cm$^2$ was placed on the specimen and left in this state for 2 minutes. After 3, 5, 7, 9, and 11 minutes respectively, measurements were made by use of an autographic recorder AG-D (a computer measurement and control type universal testing machine) manufactured by Shimadzu Corporation. As for the measuring method, the measurement was carried out in accordance with JIS K7203. As testing conditions, the inter-fulcrum distance was set at 5 cm, the area of each test piece was 100 cm$^2$, the testing speed or rate was set at 25 mm/min, and the chart speed or rate was set at 25 mm/min.

Compression Strength Exhibited after One Day

The water-curable supporting bandage was dipped into water with a temperature of 20° C. at a room temperature of 20° C. for 10 seconds; and then was lightly grasped and shaken three times to swish the water off and wound, into three turns or layers, around a stainless steel pipe with a diameter of 60.5 mm around which a release paper was previously wound. After the winding of the bandage was completed, the operator rotated the thus wound bandage by holding it with both hands and further rubbed the surface of the bandage. After 15 minutes, the bandage was dram out from the stainless steel pipe, taking care to ensure that the bandage would not be deformed. After being left to stand in a constant-temperature device of 20° C. for one day, the bandage was compressed in the radial direction by a compression test machine (the crosshead speed: 25 mm/min), and the stress when the bandage was deformed by 5 mm was measured.

TABLE 1

| Name | Contents | |
| --- | --- | --- |
| Polyol components | | |
| PEG 400 | Sanyo Chemical Industries, Ltd., Trade name PEG 400 | (Average molecular weight 400) |
| PEG 700 | Sanyo Chemical Industries, Ltd., Trade name PEG 700 | (Average molecular weight 700) |
| PEG 2000 | Sanyo Chemical Industries, Ltd., Trade name PEG 2000 | (Average molecular weight 2000) |
| PEG 4000 | Sanyo Chemical Industries, Ltd., Trade name PEG 4000S | (Average molecular weight 3300) |
| BP-23 | Sanyo Chemical Industries, Ltd., Trade name Newpol BP-23P | (Average molecular weight 360) |
| BP-600 | Sanyo Chemical Industries, Ltd., Trade name Newpol BP-600 | (Average molecular weight 600) |
| BPE-20 | Sanyo Chemical Industries, Ltd., Trade name Newpol BPE-20 | (Average molecular weight 360) |
| BPE-180 | Sanyo Chemical Industries, Ltd., Trade name Newpol BPE-180 | (Average molecular weight 1000) |
| PPG-400 | Sanyo Chemical Industries, Ltd., Trade name PPG 400 | (Average molecular weight 400) |
| Polyisocyanate components | | |
| MDI | Dow Mitsubishikasei Limited Trade name Isonate 125 M | |
| Modified MDI | Dow Mitsubishikasei Limited Trade name Isonate 143 L | |
| Catalyst | | |
| BDM | Bis-4-(2,6-dimethylmolpholine)ethylether | |

TABLE 1-continued

| Name | Contents |
|---|---|
| Stabilizer | |
| MSA | Methanesulfonic acid |
| Anti-foaming agent | |
| Byk | BYK-Chemie Japan KK Trade name Byk-A525 |

TABLE 2

| | Embodiments | | | | | Comparative Examples | | | |
|---|---|---|---|---|---|---|---|---|---|
| | 1 | 2 | 3 | 4 | 5 | 1 | 2 | 3 | 4 |
| Content of the PEG and the bisphenol system diol in the polyol components | 100 | 100 | 100 | 100 | 50 | 0 | 33 | 100 | 100 |
| Ratio of the bisphenol system diol | 0.63 | 1.04 | 0.36 | 3.1 | 0.68 | | 0.25 | 0 | 0.15 |
| Polyol | | | | | | | | | |
| PEG 400 | 53 | 95 | | 39 | 26 | | 20 | 248 | 120 |
| 700 | 110 | | 218 | | 55 | | 50 | | 155 |
| 2000 | 17 | 37 | | | | | | | |
| 4000S | 60 | 60 | 59 | 60 | 30 | | 20 | 59 | 60 |
| BP 23 | 50 | | 99 | | 25 | | | | 50 |
| 600 | 100 | 200 | | | 50 | | 50 | | |
| BPE 20 | | | | 80 | | | | | |
| 180 | | | | 227 | | | | | |
| PPG 400 | | | | | 25 | 50 | 30 | | |
| 700 | | | | | 201 | 400 | 250 | | |
| Average molecular weight | 627 | 645 | 622 | 690 | 629 | 646 | 653 | 481 | 567 |
| Polyisocyanate | | | | | | | | | |
| MDI | 475 | 472 | 483 | 521 | 500 | 525 | 485 | | 479 |
| Modified MDI | 119 | 118 | 120 | 58 | 59 | 0 | | 680 | 120 |
| Catalyst BDM | 13.5 | 15 | 12 | 12 | 15.8 | 18 | 12.7 | 12.7 | 12 |
| Stabilizer MSA | 0.7 | 0.65 | 0.65 | 0.65 | 0.65 | 0.65 | 0.65 | 0.7 | 0.65 |
| Anti-foaming agent Byk | 1 | 1 | 1 | 1 | 1 | 1 | 1 | 1 | 1 |

TABLE 3

| | Embodiments | | | | | Comparative Examples | | | |
|---|---|---|---|---|---|---|---|---|---|
| | 1 | 2 | 3 | 4 | 5 | 1 | 2 | 3 | 4 |
| Viscosity (cps) | 23,500 | 23,000 | 21,400 | 22,500 | 20,700 | 21,400 | 22,000 | 24,3000 | 20,700 |
| Storage stability (hours) | 76 | 75 | 74 | 76 | 59 | 52 | 55 | 41 | 42 |

TABLE 4

| | Embodiments | | | | | Comparative Examples | | | |
|---|---|---|---|---|---|---|---|---|---|
| | 1 | 2 | 3 | 4 | 5 | 1 | 2 | 3 | 4 |
| Working time (minutes, seconds) | 2'15" | 2'22" | 2'25" | 2'18" | 2'30" | 2'25" | 2'15" | 1'15" | 2'30" |
| Temperature when heat is generated (°C.) | 38.1 | 39.8 | 39.9 | 38.8 | 39.8 | 38 | 38.7 | 42.5 | 41.3 |
| Strength after the lapse of time | | | | | | | | | |
| 3 minutes (kg) | 2.3 | 2.1 | 2.1 | 2.2 | 2.0 | 1.6 | 1.7 | 2.0 | 2.0 |
| 5 minutes (kg) | 11.2 | 10.3 | 10.7 | 10.5 | 7.7 | 4.1 | 5.4 | 5.3 | 5.5 |
| 7 minutes (kg) | 17.8 | 16.5 | 17.0 | 16.8 | 12.3 | 7.1 | 8.3 | 8.2 | 8.7 |
| 9 minutes (kg) | 20.2 | 18.8 | 17.2 | 19.0 | 14.8 | 8.2 | 12.0 | 9.8 | 10.7 |
| 11 minutes (kg) | 22.5 | 21.3 | 22.7 | 20.1 | 16.4 | 8.9 | 14.1 | 10.9 | 11.3 |
| Strength after one day | 9.9 | 8.9 | 9 | 10.9 | 9.4 | 9.5 | 10.1 | 7.8 | 8.5 |

FIG. 1 shows the relationship between the strength exhibited by the water-curable supporting bandages and the elapsed time with reference to Embodiments 1, 2 and 5 of the present invention and Comparative Examples 1, 2 and 3. In FIG. 1, the letters A, B and C stand for the characteristic curves of the Embodiments 1, 2 and 3, while the letters P, Q and R stand for the characteristic curves of the Comparative Examples 1, 2 and 3.

Embodiment 1 was constituted such that the respective components of the polyol were blended in such a manner that the sum of the PEG and the bisphenol system diol was about 100%, and the compounding ratio between the PEG and the bisphenol system diol lay within a range from about 1:0.2 to about 1:5.0. This resin composition and the resultant water-curable supporting bandage had the following advantageous characteristics: The viscosity was about 23,500 cps, so that the resin composition could be applied to the base fabric at room temperature; and the resin thus applied was hard to separate from the fabric. Thus, a stabilized water-curable supporting bandage was obtained. Further, the storage stability was about 76 hours, so that the product, i.e., the water-curable supporting bandage, could be preserved for a long time, and no special storage location was needed for the preservation thereof. This water-curable supporting bandage had a working time of about 2 minutes 15 seconds and therefore sufficient time for application to the diseased part of a patient's body was provided. Additionally, this length of time was sufficiently long to allow the water-curable supporting bandage to be applied even to a complicated part of the patient's body using ordinary casting techniques. After the working time elapsed, the strength of the water-curable supporting bandage rapidly increased, it rapidly lost its plasticity, and it became possible for the bandage to retain its modeled shape. Further, the strength of the water-curable supporting bandage immediately after the lapse of the working time was about 2.3 kg, and the strength reached about 11.2 kg after about five minutes. In addition, in spite of the fact that the strength of the bandage increased by a rapid curing reaction effected after the lapse of the working time, the heat generation temperature was only about 38.1° C., so that no undesirable effect such as for instance scalding of the patient occurred. Further, after about nine minutes, the strength of the bandage was at least about 20.0 kg, and thus, it was possible for the bandage to bear body weight at least to some degree.

Embodiments 2, 3 and 4 were constituted such that of the polyol components thereof, the sum of the PEG and the bisphenol system diol was about 100%. Embodiment 5 was constituted such that of the polyol component, the sum of the PEG and the bisphenol system diol was about 50%. In each of Embodiments 2, 3, 4 and 5, the compounding ratio of the PEG and the bisphenol system diol lay within the range of from about 1:0.2 to about 1:5.0. In each of the Embodiments, the viscosity was from about 20,700 to about 23,500, so that the application of the resin was able to be performed satisfactorily, and the preservation period thereof during which the resin did not separate from the base fabric was also excellent. The storage stability of each of the Embodiments was from about 59 to about 76 hours, thus providing a sufficient storage or preservation period. Further, the working time was from about 2 minutes 15 seconds to about 2 minutes 30 seconds, which was considered to be within an ideal range. The curing reaction took place rapidly after the lapse of the working time, and as a result of which, in all of the Embodiments, the strength of the supporting bandage reached was about 7.7 kg or higher after about 5 minutes, during which period the highest heat generation temperature was about 39.9° C., which did not bring about any adverse effect. The strength after nine minutes was at least about 14 kg, and thus, all of the Embodiments could bear body weight to a relatively substantial extent. Moreover, the finished state of each of the water-curable supporting bandages was such that they still contained some moisture, but not enough so as to be uncomfortable for the patient.

Comparative Examples 1, 2, 3 and 4 were each composed so as to have a viscosity within a range from about 20,000 to about 25,000 cps and a working time within a range from about 2 to about 3 minutes for comparison with the above-discussed Embodiments of the present invention.

In particular, Comparative Example 1 was composed such that it contained no PEG and no bisphenol system diol. The viscosity of Comparative Example 1 was 21,400 cps, the working time thereof was 2 minutes 25 seconds, and it had a storage stability of 60 hours. However, the drawback of the Comparative Example 1 was that the curing reaction effected after the lapse of the working time was slow, and, after a modeling operation was performed, the strength of the supporting bandage hardly reached a sufficient value so that its thus modeled shape could be retained. That is, the strength after 5 minutes was 4.1 kg lower than 5.5 kg, and further, even after nine minutes, the strength was 8.2 kg lower than 14.0 kg; and thus, loading of body weight on the supporting bandage was largely impossible.

In Comparative Example 2, in the polyol, the sum of the PEG and the bisphenol system diol was lower than 50%. The viscosity of Comparative Example was 22,000 cps, and the working time was 2 minutes 15 seconds. In these respects, there was no problem, but the curing reaction after the lapse of the working time was slow as in the case of Comparative Example 1, and, after the supporting bandage was modeled, the thus modeled shape could not be retained, and more than 30 minutes was needed for making weight bearing possible.

In Comparative Example 3, PEG was used as the sole component of the polyol, the polyol containing no bisphenol system diol at all. In this Example, the viscosity was 24,300 cps, and the working time was 1 minute 50 seconds, which did not reach the predetermined range of time. Further, the storage stability was poor, and the heat generation temperature was as high as 42.5° C., and therefore, there was the danger that the patient's body might be scalded. The curing reaction effected after the lapse of the working time was very fast, and, in spite of the fact that the reaction was completed in a short time, the time spent until the final strength was reached was long, and the resulting water-curable supporting bandage was in a wet state, giving a sense of uncomfortability to the patient.

Comparative Example 4 was an example in which the proportion of the PEG and the bisphenol system diol in the components of the polyol was smaller than 1: 0.2. In this example, the viscosity was 20,700 cps, and the working time was 2 minutes 30 seconds. These were satisfactory values, but the other properties thereof exhibited approximately the same tendencies as in the case of Comparative Example 3 and thus, in these respects, Comparative Example 4 was unsatisfactory.

Thus, there has been shown and described a water-curable supporting bandage which fulfills all of the objects and advantages set forth above. It will be apparent to those skilled in the art, however, that many changes, modifications, variations and other uses and applications for the subject invention are possible. All such changes, modifications, variations and other uses which do not depart from the spirit and scope of the invention are deemed to be covered by the invention, which is limited only by the claims which follow.

What is claimed is:

1. A water-curable support bandage comprising a flexible fabric coated with water-curable polyurethane resin composition containing a polyurethane prepolymer consisting of a polyol, a polyisocyanate, a catalyst and a stabilizer, wherein said polyol contains a polyethylene glycol and a bisphenol system diol, the bisphenol system diol being the product of the reaction of a bisphenol and an oxide in the presence of a catalyst, and wherein the sum of the content of the polyethylene glycol and the content of the bisphenol system diol contained as components of said polyol is at least about 50 percent by weight based on the components of said polyol, the compounding proportion of the polyethylene glycol to the bisphenol system diol in the polyol component is from about 1:0.2 to about 1:5 parts by weight, said bandage is enclosed in a water-impermeable container and said bandage is hardenable by curing of said resin composition after immersion in water.

2. The water-curable support bandage according to claim 1 wherein the bisphenol system diol has a molecular weight of no more than about 800.

3. The water-curable support bandage of claim 1 wherein the flexible fabric is selected from a group consisting of knitted fabrics, woven fabrics and non-woven fabrics.

4. The water-curable support bandage of claim 3, wherein the knitted fabric comprises a raschel-knit having a thickness of from about 0.08 to about 5.0 mm and a mesh size of from about 3 to about 30 mesh/cm$^2$.

5. The water-curable support bandage of claim 1 wherein the polyol has an average molecular weight of from about 400 to about 2,000.

6. The water curable support bandage of claim 5 wherein the polyol has an average molecular weight of from about 500 to about 800.

7. The water-curable support bandage of claim 1 wherein the polyisocyanate is selected from a group consisting of 4,4'-diphenylmethane diisocyanate; 2,4-diphenylmethane diisocyanate; phenylene diisocyanate; and polymethylene polyphenylene polyisocyanate.

8. The water-curable support bandage of claim 1 wherein the compounding ratio of the polyisocyanate to the polyol is from about 2 to about 5 equivalents of the polyisocyanate per one equivalent of the polyol.

9. The water-curable support bandage of claim 8 wherein the compounding ratio of the polyisocyanate to the polyol is from about 2.5 to about 5 equivalents of the polyisocyanate per one equivalent of the polyol.

10. The water-curable support bandage of claim 1 wherein the polyurethane prepolymer has a viscosity from about 10,000 to about 50,000 centipoise.

11. The water curable support bandage of claim 10 wherein the polyurethane prepolymer has a viscosity from about 15,000 to about 40,000 centipoise.

12. The water-curable supporting bandage of claim 1 wherein the mount of catalyst is from about 0.1 to about 5.0 percent by weight of the polyurethane resin composition.

13. The water curable support bandage of claim 12 wherein the amount of catalyst is from about 0.5 to about 3 percent by weight of the polyurethane resin composition.

14. The water curable support bandage of claim 1 wherein the amount of the stabilizer is from about 0.005 to about 1 percent by weight of the polyurethane resin composition.

15. The water curable support bandage of claim 14 wherein the amount of the stabilizer is from about 0.01 to about 0.5 percent by weight of the polyurethane resin composition.

* * * * *

UNITED STATES PATENT AND TRADEMARK OFFICE
CERTIFICATE OF CORRECTION

PATENT NO. : 5,665,056
DATED : September 9, 1997
INVENTOR(S) : Nobuyasu Nakasugi and Takayuki Sekine It is certified that error appears in the above-identified patent and that said Letters Patent is hereby corrected as shown below:

Col. 3, line 40 and 41, "dimolpholinodiethhylether" should be -- dimolpholinodiethylether -- .

Col. 6, line 9, "mount" should be -- amount -- .

Col. 11, line 16, "rams" should be -- turns -- .

Col. 12, line 4, "dram" should be -- drawn -- .

Col. 12, line 36, "dram" should be -- drawn -- .

Col. 14, line 67, "I" should be -- 1 -- .

Col. 18, line 18, "mount" should be -- amount -- .

Signed and Sealed this

Thirtieth Day of December, 1997

Attest:

BRUCE LEHMAN

*Attesting Officer*  *Commissioner of Patents and Trademarks*